June 23, 1970 J. V. WALKER ET AL Plant Pat. 2,970

NAVEL ORANGE TREE

Filed Feb. 27, 1969 2 Sheets-Sheet 1

INVENTORS
JOHN V. WALKER
EVERETT R. SKAGGS
Lyon & Lyon
ATTORNEYS

United States Patent Office

Plant Pat. 2,970
Patented June 23, 1970

2,970
NAVEL ORANGE TREE

John V. Walker, 1661 N. Prospect, Porterville, Calif. 93257, and Everett R. Skaggs, Los Angeles, Calif.; said Skaggs assignor to said Walker Filed Feb. 27, 1969, Ser. No. 803,135
Int. Cl. A01h 5/08
U.S. Cl. Plt.—45 1 Claim This invention relates to a new variety of navel orange tree, the novel characteristics of which reside particularly in the early maturity of the fruit, large size and number of fruit, and the fruit's high juice content.

The new orange originated from a sport limb on a Washington navel (unpatented) in a grove near Strathmore, Calif. The limb with its large, early maturing and early coloring fruit was first discovered in 1958 by Everett R. Skaggs. Thereafter, the new variety was successfully asexually reproduced by John V. Walker and Everett R. Skaggs by budding on several Washington navel (unpatented) root stock. This resulted in several progeny trees which have continually displayed the growth and fruit characteristics typical of that found on the parent sport limb.

One of the tree's more interesting characteristics is the multiple fruit wood growth from the branches, a factor that adds to the tree's producing ability.

Figure 1:
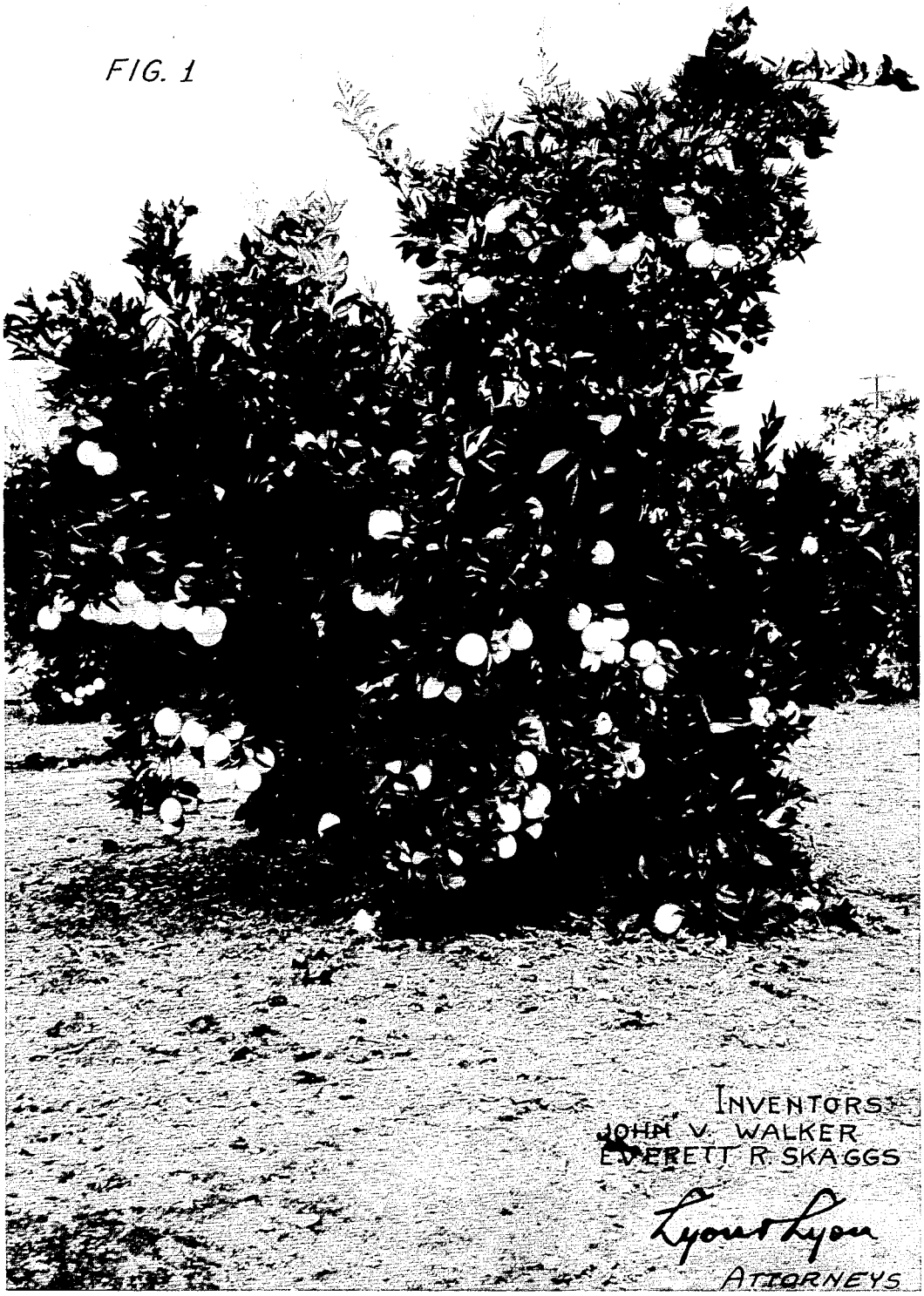
Figure 2:
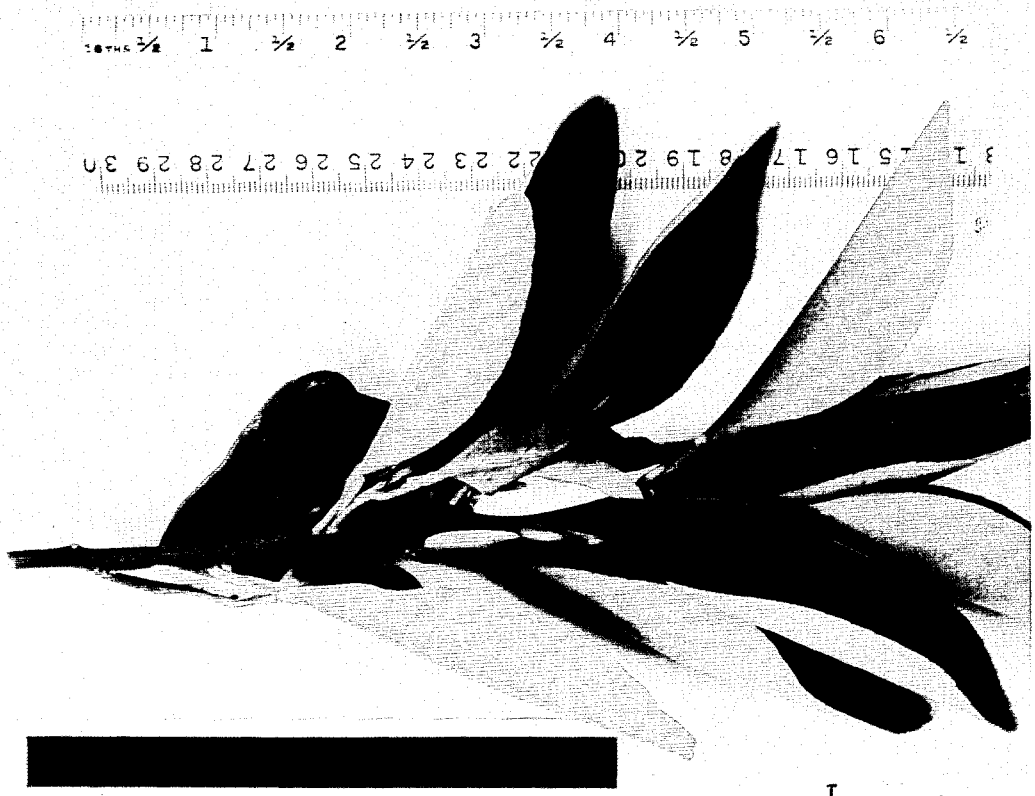

Other distinctive characteristics of the new variety are exemplified in the accompanying illustrations. FIG. 1, shows an entire tree with several clusters of fruit. FIG. 2, shows a single whole fruit of the new variety, illustrating the exterior of the fruit, a transverse mid-section of the fruit in a plane substantially perpendicular to the axis of the fruit illustrating the interior of the fruit, and portions of the stem and leaves. A measuring gauge indicates the approximate size of a mature fruit.

The following is a brief description in some detail of the new variety of orange.

Tree:

*Shape.*—Spherical to conical; somewhat drooping.

*Size.*—Medium; medium vigor.

*Growth.*—Dense; vigorous branches tend to arch prominently above and beyond the trees' general periphery; usually abundant axiallary and accessory bud development.

Flower:

*Size.*—Slightly larger than those on a Washington navel in both length and diameter.

*Season.*—About the same as those on a Washington navel.

*Ovary.*—Accelerated development following fertilization.

Leaves: shape and size—Like those on a Washington navel.

Fruit, external characters:

*Color.*—"Mandarin Orange" (color by Plochere, "A Guide to Color and Color Harmony," Plate No. 194).

*Surface.*—Finely to moderately pitted and pebbled.

*Shape.*—Spheroid to obovoid or ellipsoid; relatively symmetrical.

*Size.*—Large; diameter 80 mm.; height 76 mm.; D/H index (diameter divided by height), average 1.05.

*Base.*—Rounded or truncate to slightly collared; rugose through and slightly outside collar. Collar area slightly depressed; average diameter 8 mm.

*Calyx.*—Even to slightly depressed; size medium; irregularly divided; divisions short; sharp pointed; thick (fleshy); tips persistent.

*Stem.*—large.

*Apex.*—Flat to truncate, occasionally broadly nipled.

*Navel.*—Present; percentage navels 100; with flesh to oil cells only; size small to medium; closed percentage 2; open percentage 98; even to moderately protruding.

*Aerole.*—Indistinct.

*Stylar scar.*—Mainly disrupted by navel.

Fruit, internal characters:

*Rind.*—thickness—thin; average in median cross-section 5 mm. Firmness—Firm.—Adherence—Medium; puffing none.

*Oil glands.*—Numerous; conspicuous; 5 per one-fourth cm.

*Oil.*—Abundant; aroma medium; distinctive.

*Glandular layer.*—Medium; percentage thickness of rind 20; color orange (color by Plochere, Plate No. 145).

*Mesocarp (albedo).*—Medium; color "Yellow Gem" (color by Plochere, Plate No. 151); vascular bundles inconspicuous.

*Axis.*—Shape—in median cross-section irregular; size medium; average mid-diameter 10 mm.; average basal diameter 10 (at juncture with navel) mm.; average apical diameter 5 mm.; solid to (through) semi-hollow.

*Segments.*—Number range 9–12, average 10; adherence slight; rag from rind little; septa thin and tender; dorsal contour retuse.

*Pulp.*—Color—"Golden Rapture" (color by Plochere, Plate No. 148). Texture—fine; tender. Vesicles—small shape medium.

*Juice.*—Amount—very juicy; percentage 50. Color—"Easter Egg Yellow" (color by Plochere, Plate No. 150). Sugar—Medium; solids, percentage 11.2 (on Oct. 30, 1968). Acid—Medium; percentage 1.27 (by weight on Oct. 30, 1968); bitterness slight. Aroma—medium; attractive, Flavor—Good. Waste—from strained fruit little.

*Seeds.*—Number—very rare; imperfect seeds few.

Miscellaneous:

*Fruitfulness.*—Unusually high; tendency to clustering.

*Season.*—Very early to (through) late.

*Shipping quality.*—Good.

The above described new variety of navel orange tree retains many of the qualities of the regular Washington navel including the Washington's ease of rind removal and section (carpel) detachment, seedlessness, flavor and like the Washington navel has excellent degreening, shipping and storage characteristics. In addition, the fruits of this variety mature earlier than the Washington navel, both in rind coloring and fruit interior. Moreover, the rind coloring of the fruit is higher and the rind surface is slightly smoother textured. The tree starts fruiting earlier and the number and size of the fruit on each tree is greater, with young fruits developing unusually fast.

We claim:

1. A new and distinct variety of navel orange tree as described and illustrated, characterized particularly by its earlier maturity, its larger fruit, its greater juice content per fruit and the smoother rind surface of its fruits; all as compared with the Washington navel orange.

No references cited.

ROBERT E. BAGWILL, Primary Examiner